US008980885B2

(12) United States Patent
Soma et al.

(10) Patent No.: US 8,980,885 B2
(45) Date of Patent: Mar. 17, 2015

(54) PLANT DISEASE CONTROLLING COMPOSITION AND METHOD FOR CONTROLLING PLANT DISEASE

(75) Inventors: Masato Soma, Narashino (JP); Masanao Takaishi, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 176 days.

(21) Appl. No.: 12/934,893

(22) PCT Filed: Mar. 24, 2009

(86) PCT No.: PCT/JP2009/056426
§ 371 (c)(1),
(2), (4) Date: Dec. 29, 2010

(87) PCT Pub. No.: WO2009/119872
PCT Pub. Date: Oct. 1, 2009

(65) Prior Publication Data
US 2011/0105489 A1    May 5, 2011

(30) Foreign Application Priority Data

Mar. 28, 2008    (JP) ................................ 2008-086238

(51) Int. Cl.
| A01N 43/88 | (2006.01) |
| A01N 47/16 | (2006.01) |
| A01N 37/50 | (2006.01) |
| A01N 37/18 | (2006.01) |
| A01N 37/36 | (2006.01) |

(52) U.S. Cl.
CPC ............... *A01N 47/16* (2013.01); *A01N 37/50* (2013.01); *A01N 37/18* (2013.01); *A01N 37/36* (2013.01); *A01N 2300/00* (2013.01)
USPC ........ 514/229.2; 514/269; 514/404; 514/539; 514/622

(58) Field of Classification Search
CPC ....... A01N 47/16; A01N 37/18; A01N 37/36; A01N 37/50; A01N 2300/00
USPC ........................ 514/229.2, 269, 404, 539, 622
See application file for complete search history.

(56) References Cited

U.S. PATENT DOCUMENTS

| 5,948,819 | A  | * | 9/1999 | Ohtsuka et al. ............... 514/617 |
| 6,294,567 | B1 |   | 9/2001 | Hashizume et al. |
| 6,521,568 | B1 |   | 2/2003 | Kimura |
| 2005/0043176 | A1 |   | 2/2005 | Forster |
| 2006/0089315 | A1 | * | 4/2006 | Otsubo et al. .................. 514/22 |
| 2009/0018015 | A1 |   | 1/2009 | Wachendorff-Neumann et al. |
| 2010/0216636 | A1 |   | 8/2010 | Suty-Heinze et al. |
| 2011/0021580 | A1 | * | 1/2011 | Takaishi et al. ............... 514/352 |
| 2011/0092556 | A1 | * | 4/2011 | Soma ........................... 514/383 |
| 2011/0197318 | A1 | * | 8/2011 | Takaishi et al. ............... 800/298 |
| 2011/0269623 | A1 | * | 11/2011 | Takaishi et al. ............... 504/100 |
| 2011/0275514 | A1 | * | 11/2011 | Takaishi et al. ............... 504/100 |

FOREIGN PATENT DOCUMENTS

| CL | 2701-02 | 11/2003 |   |
| CL | 2729-04 | 12/2005 |   |
| CL | 1573-08 | 12/2008 |   |
| EP | 0 754 672 A1 | 1/1997 |   |
| EP | 1 072 598 A1 | 1/2001 |   |
| EP | 1 222 856 A1 | 7/2002 |   |
| EP | 1 652 429 A1 | 5/2006 |   |
| EP | WO2008/095890 | * 8/2008 | ............. A01N 43/56 |
| JP | 2002-316902 A | 10/2002 |   |
| WO | WO 98/43480 A1 | 10/1998 |   |

OTHER PUBLICATIONS

A.V. Sturz, M.R. Carter & H.W. Johnson, A Review of Plant Disease, Pathogen Interactions and Microbial Antagonism Under Conservation Tillage in Temperate Humid Agriculture, 41 Soil Tillage Res. 169 (1997).*
English translation of International Preliminary Report on Patentability (Form PCT/IB/373) and of Written Opinion of the International Searching Authority (Form PCT/ISA/237) issued on Sep. 28, 2010 in PCT/JP2009/056426.
European Search Report for corresponding European Patent Application No. 11162725.3, dated Jul. 12, 2012.
Official Action No. 261 for Colombian Patent Application No. 10-117827, dated Jan. 16, 2013.
Australian Examination Report, dated May 13, 2013, for Australian Application No. 2009229754.
Colombian Office Action (including partial English translation), dated Jul. 31, 2013, for Colombian Patent Application No. 13-134977-1.
The Office Action (including English translation), dated Dec. 20, 2013, issued in the corresponding Chilean Patent Application No. 707-2009.
International Search Report dated Jul. 13, 2010 in International Application No. PCT/JP2009/056426.
Kimura "Microbiocidal composition to control plant diseases in agriculture/horticulture, containing pyrazoline derivatives and other microbiocides", Database WPI Section Ch, Week 200333 Thompson Scientific, London, GB; AN 2003-345929 XP002558156.

* cited by examiner

*Primary Examiner* — Sean Basquill
(74) *Attorney, Agent, or Firm* — Birch, Stewart, Kolasch & Birch, LLP

(57) ABSTRACT

A plant disease controlling composition comprising, as active ingredients, a compound represented by the formula (I), as well as at least one compound A selected from the group consisting of dimoxystrobin, trifloxystrobin, azoxystrobin, pyraclostrobin, a compound represented by the formula (II) and an agrochemically acceptable salt of the compound represented by the formula (II): wherein, R1, Q, X, Y, Z, M and n are as defined in the description.

7 Claims, No Drawings

PLANT DISEASE CONTROLLING COMPOSITION AND METHOD FOR CONTROLLING PLANT DISEASE

TECHNICAL FIELD

The present invention relates to a plant disease controlling composition and a method of controlling a plant disease.

BACKGROUND ART

Heretofore, while various plant disease controlling agents have been developed (see e.g. WO 95/27693 A1, EP 477631 A, JP 2000-226374 A), a plant disease controlling agent having higher activity is always demanded.

DISCLOSURE OF THE INVENTION

An object of the present invention is to provide a plant disease controlling composition showing high plant disease controlling activity, and a method for effectively controlling a plant disease.

Under these circumstances, the present inventors have intensively studied and, as a result, have found that an excellent plant disease controlling effect can be obtained by applying a compound represented by the following formula (I) and a specific compound. Thus, the present invention has been completed.

That is, the present invention provides:
(i) A plant disease controlling composition comprising, as active ingredients, a compound represented by the formula (I)

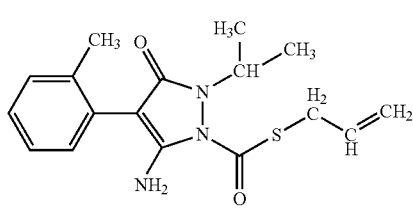

(I)

(hereinafter, referred to as the compound I in some cases), as well as at least one compound A selected from the group consisting of dimoxystrobin, trifloxystrobin, azoxystrobin, pyraclostrobin, a compound represented by the formula (II) and an agrochemically acceptable salt of the compound represented by the formula (II):

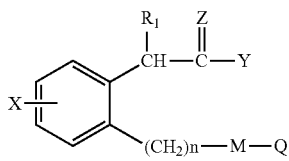

(II)

wherein, $R^1$ represents a halogen atom, an optionally substituted alkyl group, an alkoxy group, a haloalkoxy group, an alkylthio group, an alkylsulfinyl group, an alkylsulfonyl group, an optionally substituted amino group or a nitro group, Q represents an optionally substituted aryl group, an optionally substituted heterocyclic group, a mono- or di-substituted methyleneamino group, an optionally substituted alkyl group, an optionally substituted alkenyl group, an optionally substituted alkynyl group, a substituted carbonyl group or a substituted sulfonyl group, X represents a hydrogen atom, a halogen atom, an optionally substituted alkyl group, or an optionally substituted hydroxy group, Y represents an optionally substituted hydroxy group, an alkylthio group, or an optionally substituted amino group, Z represents an oxygen atom or a sulfur atom, M represents an oxygen atom, $S(O)_I$ (wherein I represents an integer of 0, 1 or 2), $NR^2$ (wherein, $R^2$ represents a hydrogen atom, an alkyl group or an acyl group) or a single bond, and n represents an integer of 0, 1 or 2 (hereinafter, referred to as the compound II in some cases) (hereinafter, referred to as the present composition in some cases); and (ii) A method for controlling a plant disease, which comprises applying the compound I as well as at least one compound A selected from the group consisting of dimoxystrobin, trifloxystrobin, azoxystrobin, pyraclostrobin, the compound II and the agrochemically acceptable salt of the compound represented by the formula (II) to a plant, a seed of a plant or a cropland (hereinafter, referred to as the present controlling method in some cases).

According to the present invention, a plant disease controlling composition showing high plant disease controlling activity, and a method for effectively controlling a plant disease can be provided.

BEST MODE FOR CARRYING OUT THE INVENTION

The compound I is described, for example, in JP 2000-226374 A. The compound can be synthesized, for example, by the method described in the aforementioned publication, or a known method.

Dimoxystrobin, trifloxystrobin, azoxystrobin, pyraclostrobin, the compound II and the salts of the compound II show inhibitory activity on an electron transport system complex III. These compounds show an effect of controlling a plant disease synergistically with the compound I.

Dimoxystrobin is a general name of (αE)-2-[(2,5-dimethylphenoxy)methyl]-α-(methoxyimino)-N-methylbenzeneacetamino, which is described in EP 477631 A.

Trifloxystrobin is a general name of methyl (E)-methoxyimino-{(E)-α-[1-(α,α,α-trifluoro-m-tolyl)ethylideneaminooxy)-o-tolyl}acetate, which is described, for example, in pages 1074 to 1075 of The Pesticide manual Fourteenth.

Azoxystrobin is a general name of methyl (E)-2-{2-[6-(2-cyanophenoxy)pyrimidin-4-yloxy]phenyl}-3-methoxyacrylate, which is described, for example, in pages 54 to 56 of The Pesticide manual Fourteenth.

Pyraclostrobin is a general name of methyl 2-[[1-(4-chlorophenyl)-1H-pyrazol-3-yloxymethyl]phenyl](N-methoxy)carbamate, which is described, for example, in pages 900 to 901 of The Pesticide manual Fourteenth.

The compound II and an agrochemically acceptable salt thereof are described in WO 95/27693 A1.

These respective compounds can be prepared by the methods described in the aforementioned publications, or a known method.

As used herein, the agrochemically acceptable salt means a salt which can be applied as an agrochemical or a starting material for an agrochemical.

The compound II is represented by the formula (II). Examples of the "halogen atom" represented by $R^1$ include fluorine, chlorine, bromine and iodine.

Examples of the "alkyl group" represented by $R^1$ include an alkyl group having 1 to 8 carbon atoms. Examples of the alkyl group include a methyl group, an ethyl group, a propyl group, an isopropyl group, a butyl group, an isobutyl group, a tert-butyl group, a pentyl group, and a hexyl group.

Among them, an alkyl group having 1 to 4 carbon atoms is preferable, and a methyl group and an ethyl group are particularly preferable.

Examples of the substituent of the "optionally substituted alkyl group" include a halogen atom (e.g. fluorine, chlorine, bromine, iodine, preferably fluorine); an alkoxy group having 1 to 8, preferably 1 to 4 carbon atoms (e.g. methoxy group, ethoxy group, propoxy group, or butoxy group).

Examples of the "substituted alkyl group" include a haloalkyl group (e.g. difluoromethyl group, trifluoromethyl group, chloromethyl group, 2-bromoethyl group, or 2,3-dichloropropyl group); and an alkoxyalkyl group (e.g. methoxymethyl group, ethoxymethyl group, or methoxyethyl group). As the haloalkyl group, a fluoroalkyl group having 1 to 4 carbon atoms is preferable, and a trifluoromethyl group is more preferable. As the alkoxyalkyl group, an alkoxyalkyl group having 1 to 3 carbon atoms in total is preferable, and a methoxymethyl group is more preferable.

Examples of the "alkoxy group" represented by $R^1$ include an alkoxy group having 1 to 8 carbon atoms, preferably, an alkoxy group having 1 to 4 carbon atoms such as a methoxy group, an ethoxy group, or a propoxy group.

Examples of the "haloalkoxy group" represented by $R^1$ include a haloalkoxy group having 1 to 8 carbon atoms, preferably a haloalkoxy group having 1 to 4 carbon atoms, more preferably a fluoroalkoxy group having 1 to 4 carbon atoms.

Examples of the "alkylthio group" represented by $R^1$ include an alkylthio group having 1 to 8, preferably 1 to 4 carbon atoms, specifically, a methylthio group, an ethylthio group, a propylthio group, and a butylthio group.

Among them, a methylthio group is preferable.

Examples of the "alkylsulfinyl group" represented by $R^1$ include an alkylsulfinyl group having 1 to 8, preferably 1 to 4 carbon atoms, specifically, a methylsulfinyl group, an ethylsulfinyl group, and a propylsulfinyl group.

Among them, a methylsulfinyl group is preferable.

Examples of the "alkylsulfonyl group" represented by $R^1$ include an alkylsulfonyl group having 1 to 8, preferably 1 to 4 carbon atoms, specifically, a methylsulfonyl group, an ethylsulfonyl group, and a propylsulfonyl group.

Among them, a methylsulfonyl group is preferable.

Examples of the "optionally substituted amino group" represented by $R^1$ include an amino group, an amino group mono- or di-substituted with an alkyl group having 1 to 8, preferably 1 to 4 carbon atoms (e.g. monomethylamino, dimethylamino, or monoethylamino), an amino group mono-substituted with a formyl group, and an amino group mono-substituted with an alkylcarbonyl group having 2 to 8, preferably 2 to 4 carbon atoms (e.g. methylcarbonylamino group). Among them, an amino group substituted with an alkyl group having 1 to 4 carbon atoms is preferable, and a monomethylamino group is particularly preferable.

Preferable examples of $R^1$ include a halogen atom, an alkyl group, a haloalkyl group, an alkoxyalkyl group, a hydroxy group, an alkoxy group, an alkenyloxy group, an alkynyloxy group, a haloalkoxy group, a haloalkenyloxy group, a haloalkynyloxy group, an alkoxyalkoxy group, an alkylcarbonyloxy group, an (alkylthio)carbonyloxy group, an alkylsulfonyloxy group, an arylsulfonyloxy group, mono- or di-alkyl-substituted carbamoyloxy group, an aryloxy group, an alkylthio group, an alkylsulfinyl group, an alkylsulfonyl group, an amino group optionally substituted with an alkyl group, a nitro group, and a tetrahydropyranyloxy group. More preferable examples include a halogen atom, a C1-C4 alkoxy group, a C1-C4 haloalkoxy group and a hydroxy group. Among them, a C1-C4 alkoxy group, and a C1-C4 haloalkoxy group are further preferable, a methoxy group, an ethoxy group, and a difluoromethyl group are particularly preferable, and a methoxy group is most preferable.

Examples of the "optionally substituted aryl group" represented by Q include an aryl group having 6 to 14 carbon atoms such as a phenyl group, and a naphthyl group.

When the aryl group is substituted, examples of the substituent include a lower alkyl group (e.g. methyl group, ethyl group, propyl group, or butyl group), a lower alkenyl group (e.g. vinyl group, allyl group, or crotyl group), a lower alkynyl group (e.g. ethynyl group, propargyl group, or butynyl group), a cycloalkyl group (e.g. cyclopropyl group cyclopentyl group, or cyclohexyl group), an lower alkoxy lower alkyl group (e.g. methoxymethyl group, ethyoxymethyl group, or 2-methoxyethyl group), cycloalkenyl group (e.g. cyclopentenyl group, or cyclohexenyl group), a lower alkanoyl group (e.g. acetyl group, propionyl group, or isobutyryl group), a lower alkylsilyl group (e.g. trimethylsilyl group, triethylsilyl group, tripropylsilyl group, or tributylsilyl group), a halo(lower)alkyl group (e.g. difluoromethyl group, trifluoromethyl group, chloromethyl group, 2-bromoethyl group, or 2,3-dichloropropyl group), a di(lower)alkylamino group (e.g. dimethylamino group, or diethylamino group), a phenyl group, a phenyl(lower)alkyl group (e.g. benzyl group, or phenethyl group), a phenyl(lower)alkenyl group (e.g. styryl group, or cinnamyl group), a furyl(lower)alkyl group (e.g. 3-furylmethyl group, or 2-furylethyl group), a furyl(lower)alkenyl group (e.g. 3-furylvinyl group, or 2-furylallyl group), a halogen atom (e.g. fluorine, chlorine, bromine, iodine), a nitro group, a cyano group, a lower alkylthio group (e.g. methylthio group, ethylthio group, or propylthio group), a lower alkoxycarbonyl group (e.g. methoxycarbonyl group, ethoxycarbonyl group, or propoxycarbonyl group), a formyl group, an amino group, a mono(lower)alkylamino group (e.g. methylamino group, or ethylamino group), —OR [wherein R is a hydrogen atom, a lower alkyl group (e.g. methyl group, ethyl group, propyl group, or butyl group), a lower alkenyl group (e.g. vinyl group, allyl group, or crotyl group), a lower alkynyl group (e.g. ethynyl group, 2-propynyl group, or 3-butynyl group), a halo(lower)alkyl group (e.g. difluoromethyl group, trifluoromethyl group, chloromethyl group, 2-bromoethyl group, or 2,3-dichloropropyl group), a lower alkanoyl group (e.g. acetyl group, propionyl group, or butyryl group), a phenyl group, a lower alkoxyphenyl group (e.g. 3-methoxyphenyl group, or 4-ethoxyphenyl group), a nitrophenyl group (e.g. 3-nitrophenyl group, or 4-nitrophenyl group), a phenyl(lower)alkyl group (e.g. benzyl group, phenethyl group, phenylpropyl group), a cyanophenyl(lower)alkyl group (e.g. 3-cyanophenylmethyl group, or 4-cyanophenylethyl group), a benzoyl group, a tetrahydropyranyl group, a pyridyl group, a trifluoromethylpyridiyl group, a pyrimidinyl group, a benzothiazolyl group, a quinolyl group, a benzoyl (lower)alkyl group (e.g. benzoylmethyl group, or benzoylethyl group), a benzenesulfonyl group, or a lower alkylbenzenesulfonyl group (e.g. toluenesulfonyl group)], and —CH$_2$-G-R' [wherein G is —O—, —S—, or —NR"— (wherein R" is a hydrogen atom or a lower alkyl group), and R' is a phenyl group, a halophenyl group (e.g. 2-chlorophenyl group, or 4-fluorophenyl group), a lower alkoxyphenyl group (e.g. 2-methoxyphenyl group, or 4-ethoxyphenyl group), a pyridyl group, or a pyrimidinyl group].

These substituents may be at any possible positions of the ring. The number of the substituents is 1 to 5, preferably 1 to 4, further preferably 1 to 3. When there are plural substituents, these may be the same or different.

As used herein, the term "lower" means 1 to 8, preferably 1 to 6, more preferably 1 to 4 carbon atoms.

The "optionally substituted aryl group" represented by Q is preferably an optionally substituted phenyl group, more preferably a phenyl group optionally substituted with a halogen atom, a methyl group, a trifluoromethyl group or a methoxy group, further preferably a 2,5-dimethylphenyl group.

Examples of the "optionally substituted heterocyclic group" represented by Q include a 5- to 7-membered heterocyclic group containing 1 to 4 hetero atoms selected from nitrogen, oxygen and sulfur as ring constituting atom(s). These heterocyclic groups may form a fused ring with another heterocycle or a benzene ring.

Specifically, examples thereof include a pyridyl group (e.g. pyridin-2-yl group, pyridin-3-yl group), a pyrimidinyl group (e.g. pyrimidin-4-yl group, pyrimidin-2-yl group), a quinolyl group (e.g. quinolin-4-yl group), a quinazolinyl group (e.g. quinazolin-4-yl group), a benzothiazolyl group (e.g. benzothiazol-2-yl group), and a pyrazolyl group (e.g. pyrazol-5-yl group), each being optionally substituted.

Among them, an optionally substituted pyridyl group is preferable.

When these heterocyclic groups are substituted, examples of the substituent include groups exemplified as those of the aryl group represented by Q.

Among them, a halogen atom, a halo(lower)alkyl group, an alkoxy group, an alkoxycarbonyl group and a formyl group are preferable, a halogen atom and a C1-C4 fluoroalkyl group are more preferable, and a chlorine atom and a trifluoromethyl group are further preferable.

These substituents may be at any possible position(s) of the heterocycle. The heterocycle has 1 to 5, preferably 1 to 4, further preferably 1 to 3 substituents. When there are plural substituents, these may be the same or different.

The "mono-substituted or di-substituted methyleneamino group" represented by Q, is represented, for example, by the formula (a):

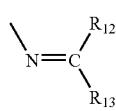
(a)

wherein $R^{12}$ and $R^{13}$ represent independently a hydrogen atom, an optionally substituted alkyl group, an acyl group, an alkylthio group, an alkylsulfinyl group, an alkylsulfonyl group, an optionally substituted amino group, a cycloalkyl group, an optionally substituted aryl group, or an optionally substituted heterocyclic group, or $R^{12}$ and $R^{13}$ together form a monocycle or a polycycle optionally containing hetero atom(s) (provided that, the case where $R^{12}$ and $R^{13}$ are a hydrogen atom at the same time is excluded)].

In the formula (a), examples of the "optionally substituted alkyl group" represented by $R^{12}$ or $R^{13}$ include the same groups as the "alkyl group" or the "substituted alkyl group" represented by the aforementioned $R^1$. Among them, a methyl group and an ethyl group are preferable.

Examples of the "acyl group" represented by $R^{12}$ or $R^{13}$ include an alkylcarbonyl group, and an arylcarbonyl group. Examples of the alkylcarbonyl group include a (C1-C6 alkyl) carbonyl group, preferably a (C1-C4 alkyl)carbonyl group such as an acetyl group, a trifluoroacetyl group, a propionyl group, and a butyryl group. Examples of the arylcarbonyl group include a (C6-C14 aryl)carbonyl group such as a benzoyl group, and a naphthoyl group.

Examples of the "alkylthio group", "alkylsulfinyl group", "alkylsulfonyl group" and "optionally substituted amino group" represented by $R^{12}$ or $R^{13}$ include those referred to as $R^1$.

Examples of the "cycloalkyl group" represented by $R^{12}$ or $R^{13}$ include a cycloalkyl group having 3 to 7, preferably 5 to 6 carbon atoms, specifically, a cyclopropyl group, a cyclobutyl group, a cyclopentyl group, a cyclohexyl group, and a cycloheptyl group.

Examples of the "optionally substituted aryl group" represented by $R^{12}$ or $R^{13}$ include a C6-C14 aryl group, specifically, a phenyl group, a naphthyl group (1-naphthyl group), and a fluorenyl group. Among them, a phenyl group is preferable.

The aryl group may be substituted at any possible position of the ring thereof, and the number of substituents is 1 to 3. Examples of the substituent include a halogen atom, an optionally substituted alkyl group, an optionally substituted hydroxy group, an alkylthio group, an optionally substituted amino group, a nitro group, a phenyl group, and a cyano group.

Examples of the halogen atom as the substituent of the "optionally substituted aryl group" represented by $R^{12}$ or $R^{13}$ include fluorine, chlorine, bromine, and iodine.

Examples of the optionally substituted alkyl group as the substiuent of the "optionally substituted aryl group" represented by $R^{12}$ or $R^{13}$ include the same group as the "optionally substituted alkyl group" represented by $R^1$. Among them, an alkyl group or a haloalkyl group is preferable, and a methyl group or a trifluoromethyl group is particularly preferable.

Examples of the optionally substituted hydroxy group as the substituent of the "optionally substituted aryl group" represented by $R^{12}$ or $R^{13}$ include a hydroxy group, an alkoxy group, an alkenyloxy group, an alkynyloxy group, a haloalkoxy group, and an aryloxy group.

Examples of the alkoxy group include an alkoxy group having 1 to 8, preferably 1 to 4 carbon atoms, specifically, a methoxy group, an ethoxy group, a propoxy group, and a butoxy group. Among them, a methoxy group is preferable.

Examples of the alkenyloxy group include an alkenyloxy group having 2 to 8, preferably 2 to 4 carbon atoms, specifically, a vinyloxy group, an allyloxy group, and a crotyloxy group. Among them, an allyloxy group is preferable.

Examples of the alkynyloxy group include an alkynyloxy group having 2 to 8, preferably 2 to 4 carbon atoms, specifically, an ethynyloxy group, a propargyloxy group, and a butynyloxy group. Among them, a propargyloxy group is preferable.

Examples of the haloalkoxy group include the aforementioned alkoxy group substituted with at least one halogen atom (e.g. fluorine, chlorine, bromine, iodine), specifically, a difluoromethoxy group, a trifluoromethyl group, and a chloromethoxy group. Among them, a difluoromethoxy group is preferable.

Examples of the aryloxy group include an aryloxy group having 6 to 12, preferably 6 to 8 carbon atoms, specifically, a phenoxy group, and a naphthoxy group.

Examples of the alkylthio group as the substituent of the "optionally substituted aryl group" represented by $R^{12}$ or $R^{13}$ include an alkylthio group having 1 to 8, preferably 1 to 4, further preferably 1 to 2 carbon atoms.

Examples of such alkylthio group include, specifically, a methylthio group, an ethylthio group, a propylthio group, and a butylthio group. Among them, a methylthio group is preferable.

Examples of the optionally substituted amino group as the substituent of the "optionally substituted aryl group" represented by $R^{12}$ or $R^{13}$ include an amino group, and an amino group mono- or di-substituted with an alkyl group having 1 to 8, preferably 1 to 4 carbon atoms (e.g. monomethylamino group, dimethylamino group, or monoethylamino group).

Examples of the "optionally substituted heterocyclic group" represented by $R^{12}$ or $R^{13}$ include a heterocyclic group containing 1 to 4, preferably 1 to 2 hetero atoms (e.g. oxygen, nitrogen, sulfur) in a ring. These heterocyclic groups may have a bond at any possible position of the ring. Examples of the heterocyclic group include a pyridyl group, a pyridazinyl group, a pyrazolyl group, a pyrimidinyl group, a furyl group, a thienyl group, an oxazolyl group, an isoxazolyl group, a benzothiazolyl group, a quinolyl group, a quinazolinyl group, a pyrazinyl group, a morpholino group, and a piperazinyl group. Among them, a furyl group (e.g. 2-furyl group), a thienyl group (e.g. 2-thienyl group), a pyridyl group (e.g. 2-pyridyl group), a pyrazinyl group (e.g. 2-pyrazinyl group), a pyrimidinyl group (e.g. 2-pyrimidinyl group), and a morpholino group are preferable. The heterocyclic group may be substituted, and examples of the substituent include the same group as the substituent of the "optionally substituted aryl group" represented by $R^{12}$ or $R^{13}$.

The "monocycle or polycycle formed by binding of $R^{12}$ or $R^{13}$, optionally containing a hetero atom" is a 4- to 8-membered ring optionally containing a hetero atom (e.g. oxygen, nitrogen, sulfur), which is formed by $R^{12}$ or $R^{13}$ together with a carbon atom to which they bind. The ring may form a fused ring with another ring. Examples of the ring include cyclopentane, cyclohexane, indane, 1,2,3,4-tetrahydronaphthalene, 5,6,7,8-tetrahydroquinoline, and 4,5,6,7-tetrahydrobenzo[b]furan. These rings may have a divalent bond at any possible position thereof.

Examples of the alkyl group of the "optionally substituted alkyl group" represented by Q include the alkyl group represented by the aforementioned $R^1$.

Examples of the alkyeyl group of the "optionally substituted alkenyl group" represented by Q include an alkenyl group having 2 to 8, preferably 3 to 6 carbon atoms, specifically, an allyl group, a propenyl group, an isopropenyl group, a butenyl group, an isobuteyl group, a pentenyl group, a hexenyl group, and a hexadienyl group.

Examples of the alkynyl group of the "optionally substituted alkynyl group" represented by Q include an alkynyl group having 2 to 6, preferably 2 to 4 carbon atoms, specifically, a propargyl group, an ethynyl group, and a butynyl group. Examples of the substituent when these alkyl group, alkenyl group, and alkynyl group are substituted include a halogen atom, an alkoxy group, an alkylthio group, an alkylsulfinyl group, an alkylsulfonyl group, and an substituted amino group, each being referred to as $R^1$, as well as an optionally substituted phenyl group, an optionally substituted naphthly group, and an optionally substituted heterocyclic group, each being referred to as Q.

Examples of the "substituted carbonyl group" represented by Q include an alkylcarbonyl group, a phenylcarbonyl group, a naphthylcarbonyl group, and a carbonyl group bonded with a heterocyclic group.

Examples of the "substituted sulfonyl group" represented by Q include an alkylsulfonyl group, a phenylsulfonyl group, a naphthylsulfonyl group, and a sulfonyl group bonded with a heterocyclic group.

The substituent in the "substituted sulfonyl group" and the "substituted carbonyl group" may further have substituent(s). For example, each alkyl group in the alkylcarbonyl group and the alkylsulfonyl group may be substituted.

Examples of the substituent in the "substituted carbonyl group" and the "substituted sulfonyl group" represented by Q include an optionally substituted alkyl group, an optionally substituted phenyl group, an optionally substituted naphthyl group, and an optionally substituted heterocyclic group.

Examples of the "optionally substituted alkyl group" in the "substituted carbonyl group" or the "substituted sulfonyl group" include those referred to as $R^1$.

Examples of the optionally substituted phenyl group, the optionally substituted naphthyl group, and the optionally substituted heterocyclic group in the "substituted carbonyl group" or the "substituted sulfonyl group" include those referred to as Q, respectively.

In the present invention, Q is preferably an optionally substituted phenyl group, more preferably a phenyl group optionally substituted with a halogen atom, a methyl group, a trifluoromethyl group or a methoxy group, further preferably a phenyl group, a 2-methylphenyl group, or a 2,5-dimethylphenyl group, particularly preferably a 2,5-dimethylphenyl group.

X represents a hydrogen atom, a halogen atom, an optionally substituted alkyl group, or an optionally substituted hydroxy group. That is, a phenylene group in the formula (II) may be unsubstituted (when X is a hydrogen atom), or may be substituted at any position with a substituent selected from a halogen atom, an optionally substituted alkyl group and an optionally substituted hydroxy group.

Examples of the "halogen atom" or the "optionally substituted alkyl group" represented by X include those referred to as $R^1$.

Examples of the "optionally substituted hydroxy group" represented by X include a hydroxy group, an optionally substituted alkoxy group, an optionally substituted alkenyloxy group, an optionally substituted alkynyloxy group, an alkylcarbonyloxy group, an (alkylthio)carbonyloxy group, an alkylsulfonyloxy group, an arylsulfonyloxy group, a mono- or di-alkyl-substituted carbamoyloxy group, an aryloxy group, and a tetrahydropyranyloxy group.

Examples of the substituent of the "optionally substituted hydroxy group" include an alkyl group, an alkenyl group, an alkynyl group, an (alkylthio)carbonyl group, an alkylcarbonyl group, an alkylsulfonyl group, an arylsulfonyl group, a mono- or di-alkyl-substituted carbamoyl group, an aryl group, and a tetrahydropyranyl group. Among these groups, an alkyl group, an alkenyl group and an alkynyl group may be substituted with a halogen atom (e.g. fluorine, chlorine, bromine, iodine, preferably fluorine), or an alkoxy group having 1 to 8, preferably 1 to 4 carbon atoms.

X is preferably a hydrogen atom.

Examples of the "optionally substituted hydroxy group" represented by Y include those referred to as X.

Examples of the "alkylthio group" represented by Y include those referred to as $R^1$.

The "optionally substituted amino group" represented by Y is represented, for example, by the formula (III):

—NR⁵R⁶ (III)

wherein $R^5$ represents a hydrogen atom or an alkyl group; $R^6$ represents a hydrogen atom, an alkyl group or a hydroxylalkyl group.

Examples of the "alkyl group" represented by $R^5$ or $R^6$, and the "alkyl group" of the "hydroxylalkyl group" represented by $R^6$ include those referred to as $R^1$. Preferably, $R^5$ and $R^6$, which are the same or different, are a hydrogen atom or an alkyl group (preferably methyl group).

Examples of Y include preferably a C1-C3 alkoxy group and a group represented by the formula (III), further preferably a methoxy group or a mono C1-C3 alkylamino group (preferably, monomethylamino group).

Z is preferably an oxygen atom.

M is preferably an oxygen atom, a sulfur atom or $NR^2$ ($R^2$ represents a hydrogen atom, an alkyl group or an acyl group), further preferably an oxygen atom.

Examples of the "alkyl group" represented by $R^2$ include those referred to as $R^1$.

Among them, a methyl group is preferable.

Examples of the "acyl group" represented by $R^2$ include a formyl group; an alkylcarbonyl group containing an alkyl group having 1 to 8, preferably 1 to 4 carbon atoms (e.g. acetyl group, propionyl group, butyryl group); a benzoyl group.

Among them, an acetyl group is preferable.

n is preferably 0 or 1, more preferably 1.

In the present invention, the preferable compound II is represented by the formula (II), wherein, $R^1$ is a halogen atom, a C1-C4 alkoxy group, or a C1-C4 haloalkoxy group, Q is a phenyl group optionally substituted with at least one substituent selected from the group consisting of a halogen atom, a methyl group, a trifluoromethyl group and a methoxy group, X is a hydrogen atom, Y is an amino group optionally substituted with at least one C1-C3 alkyl group, or a C1-C4 alkoxy group, Z is an oxygen atom, M is an oxygen atom, and n is an integer of 1.

A more preferable compound is represented by the formula (II), wherein, $R^1$ is a methoxy group, an ethoxy group or a difluoromethoxy group, Q is a phenyl group, a 2-methylphenyl group or a 2,5-dimethylphenyl group, X is a hydrogen atom, Y is a methylamino group or a methoxy group, Z is an oxygen atom, M is an oxygen atom, and n is an integer of 1.

A further preferable compound is represented by the formula (II), wherein, $R^1$ is a methoxy group, Q is a 2,5-dimethylphenyl group, X is a hydrogen atom, Y is a methylamino group, Z is an oxygen atom, M is an oxygen atom, and n is an integer of 1.

Each of the compound represented by the formula (II) and an agrochemically acceptable salt thereof includes one or more kinds of stereoisomers such as an optical isomer, and a geometric isomer based on an asymmetric carbon atom and a double bond, in some cases. Such isomers and a mixture thereof all fall within the scope of the present invention.

Some of the compound represented by the formula (II) and an agrochemically acceptable salt thereof take forms of solvates (e.g. hydrate). These forms fall within the scope of the present invention.

Some of the compound represented by the formula (II) and a salt thereof take crystal forms and/or amorphous forms, and these forms fall within the scope of the present invention.

Hereinafter, among the compound II, the compound II-i has a R-type steric structure according to Cahn Ingold-Prelog rule, wherein $R^1$ is a methoxy group, X is a hydrogen atom, Y is a methylamino group, Z is an oxygen atom, M is an oxygen atom, Q is a 2,5-dimethylphenyl group, and n is an integer of 1, which is represented by the following formula (IIa).

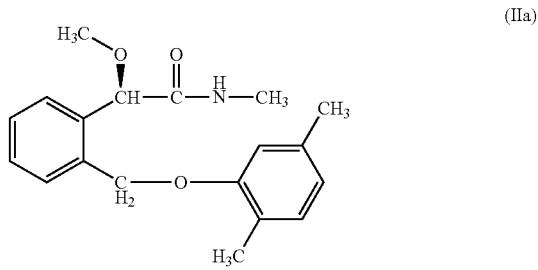 [SMILES: CNC(=O)[C@H](OC)c1ccccc1COc1cc(C)ccc1C]

(IIa)

In addition, among the compound II, the compound II-ii is a racemate, wherein $R^1$ is a methoxy group, X is a hydrogen atom, Y is a methylamino group, Z is an oxygen atom, M is an oxygen atom, Q is a 2,5-dimethylphenyl group, and n is an integer of 1, which is represented by the following formula (IIb).

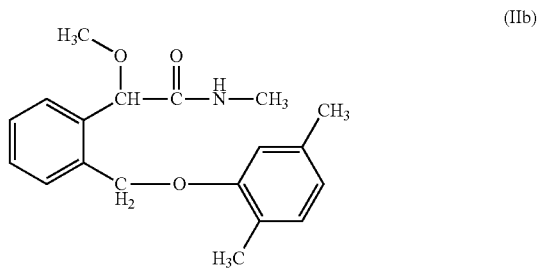 [SMILES: CNC(=O)C(OC)c1ccccc1COc1cc(C)ccc1C]

(IIb)

In the present composition, in addition to the compound (I) and the compound A, a compound which inhibits an electron transport complex III such as fluoxastrobin ((E)-{2-[6-(2-chlorophenoxy)-5-fluoropyrimidin-4-yloxy]phenyl}(5,6-dihydro-1,4,2-dioxadin-3-yl)methanone O-methyloxime), metominostrobin ((E)-2-methoxyimino-N-methyl-2-(2-phenoxyphenyl)acetamide), and pyribencarb may be added as far as it does not adversely affect the characteristics of the present invention.

The present invention can be used for farmlands, i.e., cropland, or non-farmlands such as dry field, paddy field, turf and fruit orchard. In addition, the present invention can be used for controlling diseases of "crops" such as those listed below without giving phytotoxicity to the crops.

Agricultural crops: corn, rice, wheat, barley, rye, oat, sorghum, cotton, soybean, peanut, buckwheat, sugar beet, rapeseed, sunflower, sugar cane, and tobacco;

Vegetables: Solanaceae vegetables (e.g. eggplant, tomato, green pepper, hot pepper, and potato), Cucurbitaceae vegetables (e.g. cucumber, pumpkin, zucchini, watermelon, and melon), Cruciferae vegetables (e.g. Japanese radish, turnip, horseradish, kohlrabi, Chinese cabbage, cabbage, brown mustard, broccoli, and cauliflower), Compositae vegetables (e.g. burdock, garland chrysanthemum, artichoke, and lettuce), Liliaceae vegetables (e.g. Welsh onion, onion, garlic, and asparagus), Umbelliferae vegetables (e.g. carrot, parsley, celery, and parsnip), Chenopodiaceae vegetables (e.g. spinach, and Swiss chard), Labiatae vegetables (e.g. Japanese basil, mint, and basil), strawberry, sweat potato, yam, and aroid;

Flowers and ornamental plants;

Foliage plant;

Fruit trees: pomaceous fruits (e.g. apple, common pear,

Japanese pear, Chinese quince, and quince), stone fleshy fruits (e.g. peach, plum, nectarine, Japanese plum, cherry, apricot, and prune), citrus plants (e.g. Satsuma mandarin, orange, lemon, lime, and grapefruit), nuts (e.g. chestnut, walnut, hazel nut, almond, pistachio, cashew nut, and macadamia nut), berry fruits (e.g. blueberry, cranberry, blackberry, and raspberry), grape, persimmon, olive, loquat, banana, coffee, date, and coconut;

Trees other than fruit trees: tea, mulberry, flowering trees and shrubs, street trees (e.g. ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, and yew).

The above "crops" include those having herbicide resistance imparted by a classical breeding method, or a genetic engineering technique. Examples of the herbicide to be resisted include an HPPD inhibitor such as isoxaflutole, an ALS inhibitor such as imazethapyr or thifensulfuron-methyl; an EPSP synthesizing enzyme inhibitor; and a glutamine synthesizing enzyme inhibitor; bromoxynil.

Examples of the "crops" having herbicide resistance imparted by a classical breeding method include Clearfield™ canola resistant to an imidazolinone herbicide such as imazethapyr, and STS soybean resistant to a sulfonylurea ALS inhibitor-type herbicide such as thifensulfuron-methyl. Examples of the "crops" having herbicide resistance imparted by a genetic engineering technique include soybean, cotton, and rapeseed cultivars having resistance to glyphosate or glufosinate. Some of such corn cultivars have been already marketed under the trade name of RoundupReady™, and LibertyLink™.

The above "crops" include those having an ability to synthesize, for example, a selective toxin such as that derived from the genus *Bacillus* which ability has been imparted by a genetic engineering technique.

Examples of the toxin expressed by such a genetically modified plant include insecticidal proteins derived from *Bacillus cereus* and *Bacillus popilliae*; δ-endotoxins derived from *Bacillus thuringiensis* such as Cry1Ab, Cry1Ac, Cry1F, Cry1Fa2, Cry2Ab, Cry3A, Cry3Bb1 and Cry9C; insecticidal proteins derived from *Bacillus thuringiensis*, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl syntase; chitinase; and glucanase.

The insecticidal toxin produced by such a genetically modified plant also includes hybrid toxins of 2 or more insecticidal proteins, and toxins in which a part of amino acids constituting an insecticidal protein is deleted or modified. The hybrid toxin is made by a new combination of different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more amino acids of a natural toxin are substituted.

Examples of these toxins and recombinant plants capable of synthesizing these toxins are described in EP-A-0 374 753, WO 93/07278, WO 95/34656, EP-A-0 427 529, EP-A-451 878, and WO 03/052073.

Toxins contained in these recombinant plants gives the plants resistant to, particularly, Coleoptera pests, Diptera pests, or Lepidoptera pests.

In addition, genetically modified plants containing one or plural insecticidal pest-resistant genes and expressing one or plural toxins have been already known, and some of them are commercially available. Examples of these genetically modified plants include YieldGard™ (corn variety expressing Cry1Ab toxin), YieldGard Rootworm™ (corn variety expressing Cry3Bb1 toxin), YieldGard Plus™ (corn variety expressing Cry1Ab and Cry3Bb1 toxins), Herculex I™ (corn variety expressing phosphinothricin N-acetyltransferase (PAT) for imparting resistance to Cry1Fa2 toxin and glufosinate), NuCOTN33B (cotton variety expressing Cry1Ac toxin), Bollgard I™ (cotton variety expressing Cry1Ac toxin), Bollgard II™ (cotton variety expressing Cry1Ac and Cry2Ab toxins), VIPCOT™ (cotton variety expressing VIP toxin), NewLeaf™ (potato variety expressing Cry3A toxin), NatureGard™, Agrisure™ GT Advantage (GA21 glyphosate resistance character), Agrisure™ CB Advantage (Bt11 corn borer (CB) character), and Protecta™.

The above "crops" also include those to which the ability to produce an anti-pathogenic substance having selective activity has been imparted by a genetic engineering technique.

As examples of the anti-pathogenic substance, a PR protein is known (PRPs, EP-A-0 392 225). Such an anti-pathogenic substance and a genetically modified plant producing the same are described in EP-A-0 392 225, WO 95/33818, and EP-A-0 353 191.

Examples of the anti-pathogenic substance expressed in such the genetically modified plant include ion channel inhibitors such as sodium channel inhibitor, and calcium channel inhibitor (KP1, KP4, KP6 toxins produced by viruses are known); stilbene cynthase; bibenzyl cynthase; chitinase; glucanase; PR protein; anti-pathogenic substances produced by microorganisms such as peptide antibiotics, heterocycle-containing antibiotics, and protein factors involved in plant disease-resistance (described in WO 03/000906).

Examples of plant diseases which can be controlled by the present invention are not limited to, but include the plants and diseases thereof as follows.

Rice: rice blast (*Magnaporthe grisea*), spot leaf blight (*Cochliobolus miyabeanus*), sheath blight (*Rhizoctonia solani*), silly seedling (*Gibberella fujikuroi*); Wheat, barley, etc.: powdery mildew (*Erysiphe graminis*), red mold (*Fusarium graminearum, F. avenacerum, F. culmorum, Microdochium nivale*), rust (*Puccinia striiformis, P. graminis, P. recondite, P. hordei*), snow mold (*Typhula* sp., *Micronectriella nivalis*), loose smut (*Ustilago tritici, U. nude*), bunt (*Tilletia caries*), eyespot (*Pseudocercosporella herpotrichoides*), scald disease (*Rhynchosporium secalis*), leaf blight (*Septoria tritici*), spot blight (*Leptosphaeria nodorum*), net blotch (*Pyrenophora teres* Drechsler);

Citrus fruits: black spot disease (*Diaporthe citri*), scab (*Elsinoe fawcetti*), fruit rot (*Penicillium digitatum, P. italicum*);

Apple: blossom blight (*Monilinia mali*), decomposed disease (*Valsa ceratosperma*), powdery mildew (*Podosphaera leucotricha*), Alternaria blotch (*Alternaria alternate* apple pathotype), scab (*Venturia inaequalis*), anthrax (*Colletotrichum acutatum*), crown rot (*Phytophtora cactorum*);

Pear: scab (*Venturia nashicola, V. pirina*), purple blotch (*Alternaria alternate* Japanese pear pathotype), frogeye (*Gymnosporangium haraeanum*), fruit rot (*Phytophtora cactorum*);

Peach: brown rot (*Monilinia fructicola*), black spot disease (*Cladosporium carpophilum*), Phomopsis rot (*Phomopsis sp.*);

Grape: eastern black disease (*Elsinoe ampelina*), nights grapes rot (*Glomerella cingulata*), powdery mildew (*Uncinula necator*), rust (*Phakopsora ampelopsidis*), black rot (*Guignardia bidwellii*), downy mildew (*Plasmopara viticola*);

Persimmon: anthracnose (*Gloeosporium kaki*), brown stem rot (*Cercospora kaki, Mycosphaerella nawae*);

Cucurbit: anthracnose (*Colletotrichum lagenarium*), powdery mildew (*Sphaerotheca fuliginea*), vine blight (*Mycosphaerella melonis*), yellow vine disease (*Fusarium oxysporum*), mildew (*Pseudoperonospora cubensis*), Phytophtora rot (*Phytophthora sp.*), seedling damping-off (*Pythium sp.*);

Tomato: ring spot disease (*Alternaria solani*), leaf mold (*Cladosporium fulvum*), late blight (*Phytophthora infestans*);

Eggplant: brown spot disease (*Phomopsis vexans*), powdery mildew (*Erysiphe cichoracearum*);

Cruciferous vegetable: black spot disease (*Alternaria japonica*), vitiligo (*Cercosporella brassicae*), clubroot (*Plasmodiophora brassicae*), mildew (*Peronospora parasitica*);

Leek rust (*Puccinia allii*), soybean purpura (*Cercospora kikuchii*), eastern black disease (*Elsinoe glycines*), black spot disease (*Diaporthe phaseolorum* var. sojae), rust (*Phakopsora pachyrhizi*), plaque stalks (*Phytophthora sojae*), bean anthracnose (*Colletotrichum lindemthianum*), peanut black mildew (*Cercospora personata*), brown spot disease (*Cercospora arachidicola*), blight (*Sclerotium rolfsii*);

Pea: powdery mildew (*Erysiphe pisi*);

Potato: early blight (*Alternaria solani*), late blight (*Phytophthora infestans*), powder scab (*Spongospora subterranean f. sp. subterranea*);

Strawberry: powdery mildew (*Sphaerotheca humuli*);

Tea: net rice disease (*Exobasidium reticulatum*), disease victory (*Elsinoe leucospila*), ring leaf spot (*Pestalotiopsis sp.*), anthracnose (*Colletotrichum theaesinensis*);

Tabaco: frogeye (*Alternaria longipes*), powdery mildew (*Erysiphe cichoracearum*), anthracnose (*Colletotrichum tabacum*), mildew (*Peronospora tabacina*), black shank (*Phytophthora nicotianae*);

Sugarbeet: brown spot (*Cercospora beticola*), leaf rot (*Thanatephorus cucumeris*), root rot (*Thanatephorus cucumeris*), black root rot (*Aphanidermatum cochlioides*);

Rose: black spot (*Diplocarpon rosae*), powdery mildew (*Sphaerotheca pannosa*);

Chrysanthemum: brown spot (*Septoria chrysanthemi*-indici), white rust (*Puccinia horiana*);

Diseases caused by the genus *Pythium* of various crops (*Pythium aphanidermatum, Pythium debarianum, Pythium graminicola, Pythium irregulare, Pythium ultimum*), gray mold (*Botrytis cinerea*), white mold, Sclerotinia rot, stem, rot, crown rot (*Sclerotinia sclerotiorum, Sclerotinia minor*);

Radish: black spot disease (*Alternaria brassicicola*);

Turfgrass: dollar spot disease (*Sclerotinia homeocarpa*), brown patch disease and large patch disease (*Rhizoctonia solani*);

Banana: Sigatoka disease (*Mycosphaerella fijiensis, Mycosphaerella musicola, Pseudocercospora musae*).

The present invention exhibits a particularly high effect on gray mold, white mold, *Sclerotinia* rot, stem rot, crown rot, brown rot, blossom blight, eyespot, and scald disease of various crops, among the above plant diseases.

The weight ratio of the compound A and the compound I contained in the present composition of the invention is usually 0.025:1 to 20:1, preferably 0.05:1 to 5:1, further preferably 0.05:1 to 0.25:1 (compound A: compound I).

The present composition may consist in compound A and the compound I without addition of any other ingredients, or may form a formulation in the form of a solid or liquid formulation such as wettable powder, granulated wettable powder, flowable, granules, dry flowable, emulsifiable concentrate, aqueous liquid formulation, oil solution, smoking pesticide, and aerosol, microcapsules.

Usually, these formulations can contain 0.1 to 99% by weight, preferably 0.2 to 90% by weight of the compound A and the compound I in total.

These formulations can be prepared, for example, by mixing the compound A and the compound I with a solid carrier, a liquid carrier, a gas carrier, and a surfactant and, if necessary, adding auxiliary agents for formulations such as a binder, a dispersant, and a stabilizer.

Examples of the solid carrier include finely divided powders and particles of clays (e.g. kaolin, diatomaceous earth, synthetic hydrous silicon oxide, Fubasami clay, bentonite, or acid clay), talcs, other inorganic minerals (e.g. sericite, quartz powder, sulfur powder, active carbon, calcium carbonate, or hydrated silica), and the like. Examples of the liquid carrier include water, alcohols (e.g. methanol, or ethanol), ketones (e.g. acetone, or methyl ethyl ketone), aromatic hydrocarbons (e.g. benzene, toluene, xylene, ethylbenzene, or methylnaphthalene), aliphatic hydrocarbons (e.g. n-hexane, cylcohexanone, or kerosene), esters (e.g. ethyl acetate, or butyl acetate), nitriles (e.g. acetonitrile, or isobutylonitrile), ethers (e.g. dioxane, or diisopropyl ether), acid amides (e.g. dimethylformamide, or dimethylacetamide), and halogenated hydrocarbons (e.g. dichloroethane, trichloroethylene, or carbon tetrachloride).

Examples of the surfactant include alkylsulfates, alkylsulfonates, alkylarylsulfonates, alkyl aryl ethers and polyoxyethylenated compounds thereof, polyoxyethylene glycol ethers, polyhydric alcohol esters, and sugar alcohol derivatives.

Examples of other auxiliary agents for formulations include a binder and a dispersant, specifically, casein, gelatin, polysaccharides (e.g. starch, gum arabic, cellulose derivatives, or alginic acid), lignin derivatives, bentonite, sugars, synthetic water-soluble polymers (e.g. polyvinyl alcohol, or polyvinylpyrrolidone, polyacrylic acids), PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, and fatty acids and esters thereof.

The present composition can also be prepared, for example, by separately formulating the compound A and the compound I into different formulations by the above procedures, if necessary, further diluting each of them with water, thereafter, mixing separately prepared different formulations and dilute solutions.

In the present controlling method, respective compounds may be applied to a plant, a seed of a plant or a land where the plant is grown, simultaneously or separately.

In the present controlling method, when the compound A and the compound I are simultaneously applied to a plant, a seed of a plant or a cropland, the present composition can be applied, for example, by the following method.

The method of applying the present composition is not particularly limited, as far as the present composition can be substantially applied, and examples thereof include treatment of a plant such as foliage spraying, treatment of a land such as soil treatment, and treatment of a seed such as seed disinfection.

While the application amount of the present composition differs depending on various conditions such as a particular content ratio of the compound A and the compound I, weather conditions, formulation form, application period, application method, application place, and subject disease, subject crop, the total amount of the compound A and the compound I in the soil treatment is usually 1 to 500 g, preferably 2 to 200 g per 1000 m$^2$.

When the present composition is in the form of an emulsifiable concentrate, wettable powder, suspension, or the like, it is usually applied after diluting with water, and the concentration thereof is usually 0.0005 to 2% by weight, preferably 0.005 to 1% by weight of the compound A and the compound I in total. When the present composition is in the form of dust, granules or the like, it is usually applied as it is without dilution.

The above application amount in treatment of a seed is in the range of usually 0.001 to 10 g, preferably 0.01 to 1 g of the compound A and the compound I in total relative to 1 kg of a seed.

Further, in the present controlling method, when the compound A and the compound I are separately applied to a plant, a seed of a plant, or a cropland, both compounds may be separately applied, for example, by the above methods, and the application order of both compounds is not limited. Application methods of both compounds may be the same or different. The interval of applications between both of them is, however, preferably shorter, and desirably within one day.

The application amount of each compound differs depending on various conditions such as a particular application amount ratio of the compound A and the compound I, weather conditions, formulation form, application period, application method, application place, and subject disease, subject crop and, the total amount of the compound (A) and the compound I in the soil treatment is usually 1 to 500 g, preferably 2 to 200 g per 1000 m$^2$.

The weight ratio of the compound A and the compound I to be applied separately is usually 0.125:1 to 20:1, preferably 0.25:1 to 10:1 (the compound A: the compound I).

When both compounds are in the form of emulsifiable concentrates, wettable powders, suspensions, or the like, the concentration of each compound upon application is usually 0.0005 to 1% by weight, preferably 0.005 to 0.5% by weight, respectively, and when each compound is in the form of dust, granules or the like, it is usually applied as it is without dilution. In treatment of a seed, each of the compound A and the compound I is applied in the range of usually 0.001 to 5 g, preferably 0.01 to 0.5 g relative to 1 kg of a seed.

Furthermore, the present composition can be used simultaneously with one or more fungicides, insecticides, miticides, nematocides, herbicides, plant growth regulating agents, fertilizers or soil improvers by mixing with them or without mixing them.

The fungicides, insecticides, miticides, nematocides, herbicides, plant growth regulating agents, fertilizers or soil improvers described above can be the known ones.

Hereinafter, the present invention will be explained in more detail by the following Formulation Examples, Test Examples and Comparative Examples, but the present invention is not limited to the following Examples. In the following Examples, all the "parts" are by weight unless otherwise stated. The compound II-i and the compound II-ii are as defined above. The compound III represents dimoxystrobin, the compound IV represents trifloxystrobin, the compound V represents azoxystrobin, and the compound VI represents pyraclostrobin.

Formulation Example 1

Three parts of the compound I, 2 parts of the compound II-i, the compound II-ii, the compound III, the compound IV, the compound V or the compound VI, 14 parts of polyoxyethylene styryl phenyl ether, 6 parts of calcium dodecylbenzenesulfonate and 75 parts of xylene are thoroughly mixed to prepare each emulsifiable concentrate.

Formulation Example 2

Five parts of the compound I, 5 parts of the compound II-i, the compound II-ii, the compound III, the compound IV, the compound V or the compound VI, 35 parts of a mixture of white carbon and a polyoxyethylene alkyl ether sulfate ammonium salt (weight ratio 1:1) and 55 parts of water are mixed, and pulverized by a wet grinding method to prepare each flowable.

Formulation Example 3

Twenty parts of compound I, 1 part of the compound II-i, the compound II-ii, the compound III, the compound IV, the compound V or the compound VI, and 28.5 parts of an aqueous solution containing 1.5 parts of sorbitan trioleate and 2 parts of polyvinyl alcohol are mixed, and pulverized by a wet grinding method, 37.35 parts of an aqueous solution containing 0.05 part of xanthan gum and 0.1 part of aluminum magnesium silicate is added thereto, and 10 parts of propylene glycol is further added, followed by stirring and mixing to prepare each flowable.

Formulation Example 4

Three parts of compound I, 2 parts of the compound II-i, the compound II-ii, the compound III, the compound IV, the compound V or the compound VI, 1 part of synthetic hydrous silicon oxide, 2 parts of calcium ligninsulfonate, 30 parts of bentonite and 62 parts of kaolin clay are thoroughly ground and mixed. Water is added, and the mixture is thoroughly kneaded, granulated, and dried to prepare each granule.

Formulation Example 5

Eight parts of the compound I, 40 parts of the compound II-i, the compound II-ii, the compound III, the compound IV, the compound V or the compound VI, 3 parts of calcium ligninsulfonate, 2 parts of sodium laurylsulfate, and 45 parts of synthetic hydrous silicon oxide are thoroughly ground and mixed to prepare each water dispersible powder.

Formulation Example 6

Three parts of the compound I, 2 parts of the compound II-i, the compound II-ii, the compound III, the compound IV, the compound V or the compound VI, 85 parts of kaolin clay, and 10 parts of talc are thoroughly ground and mixed to prepare each dust formulation.

Test Example 1

A sand loam was charged into a plastic pot, and cucumber (Sagamihanjiro) was seeded, and grown in a greenhouse for 12 days. A flowable of the compound I, and a flowable comprising any one of the compound II-i, the compound II-ii, the compound III, the compound IV, the compound V and the compound VI were diluted with water separately, and they were tank-mixed to prepare a tank mix solution having each predetermined concentration. The tank mix solution was subjected to foliage spraying so that it was sufficiently adhered to a leaf surface of the cucumber. After spraying, the plant was air-dried, and a PDA medium containing hyphae of *Sclerotinia sclerotiorum* was placed on the cucumber leaf surface. After seeding, this was placed under 12° C. and the high humidity for 6 days, the controlling effect was investigated.

Separately, for comparison, each of the flowables was diluted with water to prepare a water-diluted solution of compounds I to VI having the predetermined concentration, and the similar controlling test was carried out.

Further, for calculating a effective value, an onset area rate (ratio of onset area occupied in leaf area examined) in each treatment group was determined.

The effective value was calculated by the Equation 1.

Effective value (%)=100×(A−B)/A     "Equation 1"

A: Onset area rate of non-treated group
B: Onset area rate of treated group

In general, an effective value expected in treatment by mixing given two kinds of active ingredient compounds, i.e., an expected effective value is calculated by a Colby calculation equation of the Equation 2.

E=X+Y−(X×Y)/100     "Equation 2"

X: Effective value obtained by treatment with M ppm of the compound I
Y: Effective value obtained by treatment with N ppm of the compound II, III or IV
E: Effective value expected in treatment with M ppm of the compound I and N ppm of the compound II, III or IV (expected effective value)

In addition, a synergistic effect was shown herein by a value calculated by the following Equation 3.

Synergistic effect=100×[(actual effective value)/(expected effective value)]     "Equation 3"

The results are shown in Table 1.

TABLE 1

| Test compound | Active ingredient concentration (ppm) | Actual effective value | Expected effective value | Synergistic effect |
|---|---|---|---|---|
| (Compound I) + (Compound II-i) | 3.1 + 0.2 | 86 | 64 | 134 |
| (Compound I) + (Compound II-i) | 3.1 + 0.8 | 91 | 81 | 112 |
| (Compound I) + (Compound II-ii) | 3.1 + 0.2 | 80 | 60 | 133 |
| (Compound I) + (Compound II-ii) | 3.1 + 0.8 | 86 | 71 | 121 |
| (Compound I) + (Compound III) | 3.1 + 0.2 | 83 | 62 | 134 |
| (Compound I) + (Compound IV) | 3.1 + 0.2 | 88 | 70 | 126 |
| (Compound I) + (Compound V) | 3.1 + 0.2 | 83 | 63 | 132 |
| (Compound I) + (Compound VI) | 3.1 + 0.2 | 90 | 70 | 129 |
| (Compound I) | 3.1 | 58 | — | — |
| (Compound II-i) | 0.2 | 14 | — | — |
| (Compound II-i) | 0.8 | 55 | — | — |
| (Compound II-ii) | 0.2 | 4 | — | — |
| (Compound II-ii) | 0.8 | 31 | — | — |

TABLE 1-continued

| Test compound | Active ingredient concentration (ppm) | Actual effective value | Expected effective value | Synergistic effect |
|---|---|---|---|---|
| (Compound III) | 0.2 | 9 | — | — |
| (Compound IV) | 0.2 | 28 | — | — |
| (Compound V) | 0.2 | 10 | — | — |
| (Compound VI) | 0.2 | 29 | — | — |

INDUSTRIAL APPLICABILITY

According to the present invention, it is possible to provide a plant disease controlling composition showing high plant disease controlling activity, and a method for effectively controlling a plant disease.

The invention claimed is:

1. A plant fungal disease controlling composition comprising, as active ingredients, a compound represented by the formula (I):

(I)

as well as at least one compound A selected from the group consisting of dimoxystrobin, trifloxystrobin, azoxystrobin, pyraclostrobin, a compound represented by the formula (IIa):

(IIa)

a compound represented by the formula (IIb):

(IIb)

and an agrochemically acceptable salt of the compound represented by the formula (IIa) or (IIb) wherein the weight ratio of the compound A to the compound of formula (I) is 0.025:1 to 20:1 (compound A:compound of formula (I)).

2. A method for controlling a plant fungal disease, which comprises applying a compound represented by the formula (I):

(I)

[Chemical structure of formula (I): a pyrazolone ring bearing a 2-methylphenyl group, an NH₂ group, an isopropyl N-substituent, and an N-C(=O)-S-CH₂-CH=CH₂ group]

as well as at least one compound A selected from the group consisting of dimoxystrobin, trifloxystrobin, azoxystrobin, pyraclostrobin, a compound represented by the formula (IIa):

(IIa)

[Chemical structure of formula (IIa): methoxyiminoacetamide-type strobilurin with (R) or (S) stereochemistry, N-methyl amide, and 2,5-dimethylphenoxymethyl group]

a compound represented by the formula (IIb):

(IIb)

[Chemical structure of formula (IIb): analogous strobilurin-type compound with opposite configuration]

and an agrochemically acceptable salt of the compound represented by the formula (IIa) or (IIb), to a plant, a seed of a plant or a cropland wherein the weight ratio of the compound A to the compound of formula (I) is 0.025:1 to 20:1 (compound A:compound of formula (I)).

3. The plant fungal disease controlling composition according to claim 1, wherein the compound A is dimoxystrobin, trifloxystrobin, azoxystrobin, or pyraclostrobin.

4. The plant fungal disease controlling composition according to claim 1, wherein the compound A is a compound represented by the formula (IIa) or (IIb) and an agrochemically acceptable salt thereof.

5. The method for controlling a plant fungal disease according to claim 2, wherein the plant and the plant fungal disease are selected from the group consisting of:

Rice: rice blast (*Magnaporthe grisea*), spot leaf blight (*Cochliobolus miyabeanus*), sheath blight (*Rhizoctonia solani*), silly seedling (*Gibberella fujikuroi*);

Wheat or barley: powdery mildew (*Erysiphe graminis*), red mold (*Fusarium graminearum, F. avenacerum, F. culmorum, Microdochium nivale*), rust (*Puccinia striiformis, P. graminis, P. recondita, P. hordei*), snow mold (*Typhula* sp., *Micronectriella nivalis*), loose smut (*Ustilago tritici, U. nuda*), bunt (*Tilletia caries*), eyespot (*Pseudocercosporella herpotrichoides*), scald disease (*Rhynchosporium secalis*), leaf blight (*Septoria tritici*), spot blight (*Leptosphaeria nodorum*), net blotch (*Pyrenophora teres Drechsler*);

Citrus fruits: black spot disease (*Diaporthe citri*), scab (*Elsinoe fawcetti*), fruit rot (*Penicillium digitatum, P. italicum*);

Apple: blossom blight (*Monilinia mali*), decomposed disease (*Valsa ceratosperma*), powdery mildew (*Podosphaera leucotricha*), Alternaria blotch (*Alternaria alternata* apple pathotype), scab (*Venturia inaequalis*), anthrax (*Colletotrichum acutatum*), crown rot (*Phytophtora cactorum*);

Pear: scab (*Venturia nashicola, V pirina*), purple blotch (*Alternaria alternata* Japanese pear pathotype), frogeye (*Gymnosporangium haraeanum*), fruit rot (*Phytophtora cactorum*);

Peach: brown rot (*Monilinia fructicola*), black spot disease (*Cladosporium carpophilum*), Phomopsis rot (*Phomopsis* sp.);

Grape: eastern black disease (*Elsinoe ampelina*), nights grapes rot (*Glomerella cingulata*), powdery mildew (*Uncinula necator*), rust (*Phakopsora ampelopsidis*), black rot (*Guignardia bidwellii*), downy mildew (*Plasmopara viticola*);

Persimmon: anthracnose (*Gloeosporium kaki*), brown stem rot (*Cercospora kaki, Mycosphaerella nawae*);

Cucurbit: anthracnose (*Colletotrichum lagenarium*), powdery mildew (*Sphaerotheca fuliginea*), vine blight (*Mycosphaerella melonis*), yellow vine disease (*Fusarium oxysporum*), mildew (*Pseudoperonospora cubensis*), Phytophtora rot (*Phytophthora* sp.), seedling damping-off (*Pythium* sp.);

Tomato: ring spot disease (*Alternaria solani*), leaf mold (*Cladosporium fulvum*), late blight (*Phytophthora infestans*);

Eggplant: brown spot disease (*Phomopsis vexans*), powdery mildew (*Erysiphe cichoracearum*);

Cruciferous vegetable: black spot disease (*Alternaria japonica*), vitiligo (*Cercosporella brassicae*), clubroot (*Plasmodiophora brassicae*), mildew (*Peronospora parasitica*);

Leek rust (*Puccinia allii*), soybean purpura (*Cercospora kikuchii*), eastern black disease (*Elsinoe glycines*), black spot disease (*Diaporthe phaseolorum* var. *sojae*), rust (*Phakopsora pachyrhizi*), plaque stalks (*Phytophthora sojae*), bean anthracnose (*Colletotrichum lindemthianum*), peanut black mildew (*Cercospora personata*), brown spot disease (*Cercospora arachidicola*), blight (*Sclerotium rolfsii*);

Pea: powdery mildew (*Erysiphe pisi*);

Potato: early blight (*Alternaria solani*), late blight (*Phytophthora infestans*), powder scab (*Spongospora subterranea f.* sp. *subterranea*);

Strawberry: powdery mildew (*Sphaerotheca humuli*);

Tea: net rice disease (*Exobasidium reticulatum*), disease victory (*Elsinoe leucospila*), ring leaf spot (*Pestalotiopsis* sp.), anthracnose (*Colletotrichum theae-sinensis*);

Tabaco: frogeye (*Alternaria longipes*), powdery mildew (*Erysiphe cichoracearum*), anthracnose (*Colletotrichum tabacum), mildew (*Peronospora tabacina*), black shank (*Phytophthora nicotianae*);

Sugarbeet: brown spot (*Cercospora beticola*), leaf rot (*Thanatephorus cucumeris*), root rot (*Thanatephorus cucumeris*), black root rot (*Aphanidermatum cochlioides*);

Rose: black spot (*Diplocarpon rosae*), powdery mildew (*Sphaerotheca pannosa*);

Chrysanthemum: brown spot (*Septoria chrysanthemi-indici*), white rust (*Puccinia horiana*);

Radish: black spot disease (*Alternaria brassicicola*);

Turfgrass: dollar spot disease (*Sclerotinia homeocarpa*), brown patch disease and large patch disease (*Rhizoctonia solani*); and Banana: Sigatoka disease (*Mycosphaerella fijiensis, Mycosphaerella musicola, Pseudocercospora musae*).

6. The method for controlling a plant fungal disease according to claim 2, wherein the plant fungal disease is selected from the group consisting of *Pythium aphanidermatum, Pythium debarianum, Pythium graminicola, Pythium irregulare, Pythium ultimum*, gray mold (*Botrytis cinerea*), white mold, *Sclerotinia* rot, stem, rot and crown rot (*Sclerotinia sclerotiorum, Sclerotinia minor*).

7. The method for controlling a plant fungal disease according to claim 2, wherein the plant fungal disease is selected from the group consisting of gray mold, white mold, *Sclerotinia* rot, stem rot, crown rot, brown rot, blossom blight, eyespot and scald disease.

* * * * *